United States Patent
Jung et al.

(10) Patent No.: US 11,247,051 B1
(45) Date of Patent: Feb. 15, 2022

(54) SYSTEMS AND METHODS FOR CONTROLLED PACING OF RESPIRATORY MUSCLES

(71) Applicants: Ranu Jung, Miami, FL (US); Ricardo Siu, Miami, FL (US)

(72) Inventors: Ranu Jung, Miami, FL (US); Ricardo Siu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/177,650

(22) Filed: Feb. 17, 2021

(51) Int. Cl.
*A61N 1/36* (2006.01)
*A61B 5/083* (2006.01)

(52) U.S. Cl.
CPC .......... *A61N 1/3601* (2013.01); *A61B 5/0836* (2013.01)

(58) Field of Classification Search
None
See application file for complete search history.

(56) References Cited

U.S. PATENT DOCUMENTS

| | | | |
|---|---|---|---|
| 8,617,228 B2* | 12/2013 | Wittenberger | A61B 5/389 607/96 |
| 9,398,931 B2* | 7/2016 | Wittenberger | A61B 18/1492 |
| 2009/0299430 A1* | 12/2009 | Davies | A61B 5/14546 607/22 |
| 2012/0016251 A1* | 1/2012 | Zhang | A61B 5/0836 600/532 |
| 2016/0287877 A1* | 10/2016 | Jung | A61N 1/3611 |
| 2017/0189265 A1* | 7/2017 | Freeman | A61B 5/318 |
| 2020/0406034 A1* | 12/2020 | Bhattacharya | A61N 1/371 |

OTHER PUBLICATIONS

James J. Abbas et al., Experimental Evaluation of an Adaptive Feedforward Controller for Use in Functional Neuromuscular Stimulation Systems, IEEE Transactions on Rehabilitation Engineering, vol. 5, No. 1, Mar. 1997, 11 pages.
S.M. Botros et al., Neural Network Implementation of a Three-Phase Model of Respiratory Rhythm Generation, Biol. Cybern. 63, 143-153 (1990), 11 pages.
Ricardo Siu, Adaptive Closed-Loop Neuromorphic Contoller for Use in Respiratory Pacing, Florida International University (FIU) Theses and Dissertations, Jul. 10, 2019, Part 1 of 2, pp. 1-85.
Ricardo Siu, Adaptive Closed-Loop Neuromorphic Contoller for Use in Respiratory Pacing, Florida International University (FIU) Theses and Dissertations, Jul. 10, 2019, Part 2 of 2. pp. 86-177.

(Continued)

Primary Examiner — Brian T Gedeon
(74) Attorney, Agent, or Firm — Saliwanchik, Lloyd & Eisenschenk (57) ABSTRACT

Systems and methods for providing respiratory pacing using a closed-loop adaptive controller that can self-adjust in real-time to meet metabolic needs of a subject are provided. The controller can use an adaptive pattern generator/pattern shaper architecture that can autonomously generate a desired ventilatory pattern in response to dynamic changes in arterial carbon dioxide levels and, based on a learning algorithm or machine learning, can modulate stimulation intensity and cycle duration to evoke the desired ventilatory pattern.

18 Claims, 7 Drawing Sheets

(56) References Cited

OTHER PUBLICATIONS

Ricardo Siu et a., Restoring Ventilatory Control Using an Adaptive Bioelectronic System, Journal of Neurotrauma 36:3363-3377 (Dec. 15, 2019), 15 pages.

Mallika Fairchild et al., Repetetive Hindlimb Movement Using Intermittent Adaptive Neuromuscular Electrical Stimulation in an Incomplete Spinal Cord Injury Rodent Model, National Institute of Health (NIH) Public Access, Author Manuscript, Exp Neurol. Jun. 2010; 22392): 623-633, 21 pages.

Seung-Jae Kim et al., Adaptive Control of Movement for Neuromuscular Stimulation-Assisted Therapy in a Rodent Model, HHS Public Access, Author Manuscript, IEEE Trans Biomed Eng. Feb. 2009; 56(2): 452-461, 26 pages.

* cited by examiner

| | | | | | | | | | |
|---|---|---|---|---|---|---|---|---|---|
| $r$ | 1.1 | $W_{EI}$ | 1.371 | $W_{PI}$ | 1.719 | $W_{LI}$ | 5.0 | $W_{II}$ | 0.7 |
| $W_{IL}$ | 1.361 | $W_{EL}$ | 0.793 | $W_{RL}$ | 2.056 | $W_{LL}$ | 2.3 | $W_{vL}$ | 10.5 |
| $W_{EP}$ | 1.351 | $W_{RP}$ | 2.254 | $W_{PP}$ | 1.540 | $W_{IE}$ | 0.729 | $W_{RE}$ | 2.254 |
| $W_{EE}$ | 1.550 | $W_{IR}$ | 1.80 | $W_{PR}$ | 2.150 | $W_{RR}$ | 0.650 | $W_{vR}$ | 1.05 |
| $K$ | 0.6 | $k_d$ | 7 $gcm^3/s^2$ | $K_1$ | 2.5 | $K_2$ | 4 | $m_L$ | 1.8 g |
| $B_L$ | 8.4 g/s | $K_L$ | 11.5 $g/s^2$ | $n_a$ | 17 | $n_p$ | 6 | $\eta$ | 0.001 |
| $T$ | 0.014 s | $V_T$ | 297.72 ml | $V_B$ | 2.28 ml | $M_T$ | 0.49 | $Q$ | 1.2875 ml/s |
| $Q_T$ | 1.2512 ml/s | $Q_B$ | 0.0363 ml/s | $C_{IB}$ | 0.01 | $\tau_{AT}$ | 0.027 s | $\tau_{AB}$ | 0.01 s |
| $\tau_{VT}$ | 0.1 s | $\tau_{VB}$ | 0.02 s | | | | | | |

FIG. 7

SYSTEMS AND METHODS FOR CONTROLLED PACING OF RESPIRATORY MUSCLES

GOVERNMENT SUPPORT

This invention was made with government support under R01NS086088 awarded by National Institutes of Health. The government has certain rights in the invention.

BACKGROUND

Mechanical ventilation is the de-facto approach to maintain proper ventilation when independent breathing is not possible. However, mechanical ventilation poses a risk of alveolar damage and can lead to diaphragm muscle atrophy. In turn, these factors can delay or prevent subsequent weaning from ventilatory support. Direct electrical stimulation of the diaphragm or phrenic nerve has therefore been advanced as alternative means of sustaining breathing after neuromuscular injury or disease. Diaphragm stimulation can elicit functional breaths, ameliorate atrophy, and reduce the risk of lung damage. However, the current technology for controlling a "diaphragm pacer" is not capable of automated, real time adaptations to patient needs; rather, the pacer is set manually and stimulation parameters remain fixed until further adjustment by a medical practitioner. In health, alveolar ventilation is exquisitely regulated such that arterial levels of carbon dioxide are maintained around a tight "set point" of approximately 40 mmHg. Indeed, even a 1 mmHg change in arterial $CO_2$ can cause a significant change in breathing. This tight matching of breathing with $CO_2$ delivery is required to maintain acid/base homeostasis and is a fundamental aspect of ventilatory control in humans.

BRIEF SUMMARY

In view of the shortcomings in the related art, an objective of embodiments of the subject invention is to provide a closed-loop diaphragm-pacing controller that mimics the endogenous biological controller by responding to changes in metabolic demand with appropriate changes in ventilation, but without the need for manual manipulation of pacing parameters. Embodiments of the subject invention provide novel and advantageous systems and methods for providing respiratory pacing using a closed-loop adaptive controller that can self-adjust in real-time to meet metabolic needs of a subject (e.g., a mammalian subject such as a human subject). The controller can use an adaptive pattern generator (PG)/pattern shaper (PS) (PG/PS) architecture that can autonomously generate a desired ventilatory pattern in response to dynamic changes in arterial $CO_2$ levels and, based on a learning algorithm or machine learning, can modulate stimulation intensity and cycle duration to evoke the desired ventilatory pattern. The closed-loop controller can be a bioelectronic controller and provides advances over the state-of-art in respiratory pacing by providing the ability to automatically personalize stimulation patterns and adapt to achieve adequate ventilation.

In an embodiment, a system for providing respiratory pacing to meet metabolic needs of a subject can comprise: a stimulator configured to be in operable communication with the subject; and a controller in operable communication with the stimulator and having a PG/PS architecture. The controller can comprise: a processor; and a (non-transitory) machine-readable medium in operable communication with the processor and having instructions stored thereon that, when executed by the processor, perform the following steps: a) collecting (e.g., by the processor) first data regarding an end-tidal carbon dioxide ($etCO_2$) level of the subject; b) generating (e.g., by the processor) a prescribed ventilatory pattern based on the $etCO_2$ level using at least one model on the first data; c) tuning (e.g., by the processor) pacing parameters of the stimulator such that an evoked ventilatory pattern of the stimulator is matched to the prescribed ventilatory pattern; and d) causing (e.g., by the processor) the stimulator to provide the prescribed ventilatory pattern to the subject. Steps a)-d) can be repeated for each breath of the subject while the system is in use. The at least one model can utilize machine learning, a learning algorithm, or both. The at least one model can comprise at least one of a respiratory central pattern generator (rCPG) model, a pulmonary stretch receptor (PSR) model, and a $CO_2$ chemoreceptor model (e.g., the at least one model can comprise all three of these). The chemoreceptor model can convert the $etCO_2$ level to neural $CO_2$ drive and provide the neural $CO_2$ drive to the rCPG; the rCPG can provide simulated inspiratory activity to the PSR; and/or the PSR can provide a PSR drive value to the rCPG. The causing of the stimulator to provide the prescribed ventilatory pattern to the subject can comprise causing the stimulator to provide the prescribed ventilatory pattern to the diaphragm of the subject. The pacing parameters of the stimulator may be tuned only automatically by the controller, with no manual tuning of the pacing parameters of the stimulator while the system is in use. The generating of the prescribed ventilatory pattern can comprise: generating a ventilatory response based on the $etCO_2$ level using the at least one model on the first data; and scaling the ventilatory response in amplitude by a first factor (e.g., $Kr_s$) and in time by a second factor (e.g., $Kr_t$) to generate the prescribed ventilatory pattern. Steps a)-d) can occur in real time. The instructions when executed by the processor can further perform the following steps: collecting, by the processor, second data regarding a breath volume of the subject end-tidal carbon dioxide (etCO2) level of the subject; and utilizing the second data during the tuning of the pacing parameters of the stimulator.

In another embodiment, a method for providing respiratory pacing to meet metabolic needs of a subject using a controller having a PG/PS architecture can comprise: a) collecting, (e.g., by a processor of the controller in operable communication with a stimulator configured to be in operable communication with the subject) first data regarding an $etCO_2$ level of the subject; b) generating (e.g., by the processor) a prescribed ventilatory pattern based on the $etCO_2$ level using at least one model on the first data; c) tuning (e.g., by the processor) pacing parameters of the stimulator such that an evoked ventilatory pattern of the stimulator is matched to the prescribed ventilatory pattern; and d) causing (e.g., by the processor) the stimulator to provide the prescribed ventilatory pattern to the subject. Steps a)-d) can be repeated for each breath of the subject while the method is being performed. The at least one model can utilize machine learning, a learning algorithm, or both. The at least one model can comprise at least one of an rCPG model, a PSR model, and a $CO_2$ chemoreceptor model (e.g., the at least one model can comprise all three of these). The chemoreceptor model can convert the $etCO_2$ level to neural $CO_2$ drive and provide the neural $CO_2$ drive to the rCPG; the rCPG can provide simulated inspiratory activity to the PSR; and/or the PSR can provide a PSR drive value to the rCPG. The causing of the stimulator to provide the prescribed ventilatory pattern to the subject can comprise causing the stimulator to provide the prescribed ventilatory pattern to the diaphragm of the subject. The pacing parameters of the stimulator may be tuned only automatically by the controller, with no manual tuning of the pacing parameters of the stimulator while the method is being performed. The generating of the prescribed ventilatory pattern can comprise: generating a ventilatory response based on the etCO$_2$ level using the at least one model on the first data; and scaling the ventilatory response in amplitude by a first factor (e.g., Kr$_s$) and in time by a second factor (e.g., Kr$_t$) to generate the prescribed ventilatory pattern. Steps a)-d) can occur in real time. The method can further comprise: collecting, by the processor, second data regarding a breath volume of the subject end-tidal carbon dioxide (etCO2) level of the subject; and utilizing the second data during the tuning of the pacing parameters of the stimulator.

In another embodiment, a system for providing respiratory pacing to meet metabolic needs of a subject can comprise: a stimulator configured to be in operable communication with the subject; and a controller in operable communication with the stimulator and having a PG/PS architecture. The controller can comprise: a processor; and a (non-transitory) machine-readable medium in operable communication with the processor and having instructions stored thereon that, when executed by the processor, perform the following steps: a) collecting (e.g., by the processor) first data regarding an etCO$_2$ level of the subject; b) generating (e.g., by the processor) a ventilatory response based on the etCO$_2$ level using at least one model on the first data; c) scaling (e.g., by the processor) the ventilatory response in amplitude by a first factor (e.g., Kr$_s$) and in time by a second factor (e.g., Kr$_t$) to generate a prescribed ventilatory pattern; d) collecting (e.g., by the processor) second data regarding a breath volume of the subject; e) tuning (e.g., by the processor) pacing parameters of the stimulator, utilizing the second data, such that an evoked ventilatory pattern of the stimulator is matched to the prescribed ventilatory pattern; f) causing (e.g., by the processor) the stimulator to provide the prescribed ventilatory pattern to a diaphragm of the subject. Steps a)-f) can be repeated for each breath of the subject while the system is in use. The at least one model can comprise an rCPG model, a PSR model, and a CO$_2$ chemoreceptor model. The chemoreceptor model can convert the etCO$_2$ level to neural CO$_2$ drive and provide the neural CO$_2$ drive to the rCPG; the rCPG can provide simulated inspiratory activity to the PSR; and the PSR can provide a PSR drive value to the rCPG. The pacing parameters of the stimulator may be tuned only automatically by the controller, with no manual tuning of the pacing parameters of the stimulator while the system is in use. Steps a)-f) can occur in real time.

BRIEF DESCRIPTION OF DRAWINGS

FIGS. 4a-4c show performance of the adaptive PG/PS controller of FIG. 2 assessed in the computational testbed of FIG. 3.

FIGS. 5a-5c show performance of an adaptive PG/PS controller use in vivo after anesthesia-induced hypoventilation.

FIGS. 6a-6e show performance of adaptive PG/PS use in vivo after hypoventilation following C2 spinal cord hemisection.

DETAILED DESCRIPTION

Embodiments of the subject invention provide novel and advantageous systems and methods for providing respiratory pacing using a closed-loop adaptive controller that can self-adjust in real-time to meet metabolic needs of a subject (e.g., a mammalian subject such as a human subject). The controller can use an adaptive pattern generator (PG)/pattern shaper (PS) (PG/PS) architecture that can autonomously generate a desired ventilatory pattern in response to dynamic changes in arterial CO$_2$ levels and, based on a learning algorithm or machine learning, can modulate stimulation intensity and cycle duration to evoke the desired ventilatory pattern. The closed-loop controller can be a bioelectronic controller and provides advances over the state-of-art in respiratory pacing by providing the ability to automatically personalize stimulation patterns and adapt to achieve adequate ventilation.

Mechanical ventilation is the standard treatment when volitional breathing is insufficient, but drawbacks to mechanical ventilation include muscle atrophy, alveolar damage, and reduced mobility. Respiratory pacing is an alternative approach using an electrical-stimulation-induced diaphragm contraction to ventilate the lung. Oxygenation and acid-base homeostasis are maintained by matching ventilation to metabolic needs; however, related art pacing technology requires manual tuning and does not respond to dynamic user-specific metabolic demand, thereby requiring manual re-tuning of stimulation parameters as physiological changes occur. Embodiments of the subject invention address these drawbacks of current pacing systems by autonomously generating a desired ventilatory pattern in response to dynamic changes in arterial CO$_2$ levels and modulating stimulation intensity and cycle duration to evoke the desired ventilatory pattern. Embodiments of the subject invention build upon, and provide novel and advantageous improvements to, the systems and methods described in U.S. Pat. Nos. 10,589,098 and 9,872,989, both of which are hereby incorporated by reference herein in their entireties. In vivo experiments in rats with respiratory depression and in those with a paralyzed hemidiaphragm confirmed that the controllers of embodiments of the subject invention can adapt and control ventilation to ameliorate hypoventilation and restore normocapnia regardless of the cause of respiratory dysfunction (see the Examples section herein).

In an embodiment, a neuromorphic closed-loop PG/PS adaptive controller can automatically adapt to changes in end-tidal CO$_2$ (etCO$_2$) levels expired by a subject and can prescribe a ventilatory pattern on a breath-by-breath basis. The etCO$_2$ levels are easily measured and directly correlate with arterial CO$_2$. The controller can produce, in real-time, the prescribed ventilatory pattern by modulating diaphragm muscle stimulation. The approach can enable generation of the desired dynamic volume profile within a given breath, thereby preventing or inhibiting respiratory acidosis or alkalosis if metabolic (and thus respiratory) demand changes. Embodiments provide novel schemes to self-adjust the neural components of the PS to allow changes in the duration of the respiratory cycle on a breath-by-breath basis. In an embodiment, a novel computational testbed can be used to assess a PG/PS controller in silico. The computational model can include biomechanical, muscular, and CO$_2$ dynamics and can be integrated into a testbed to assess the adaptive PG/PS controller.

Figure 1:
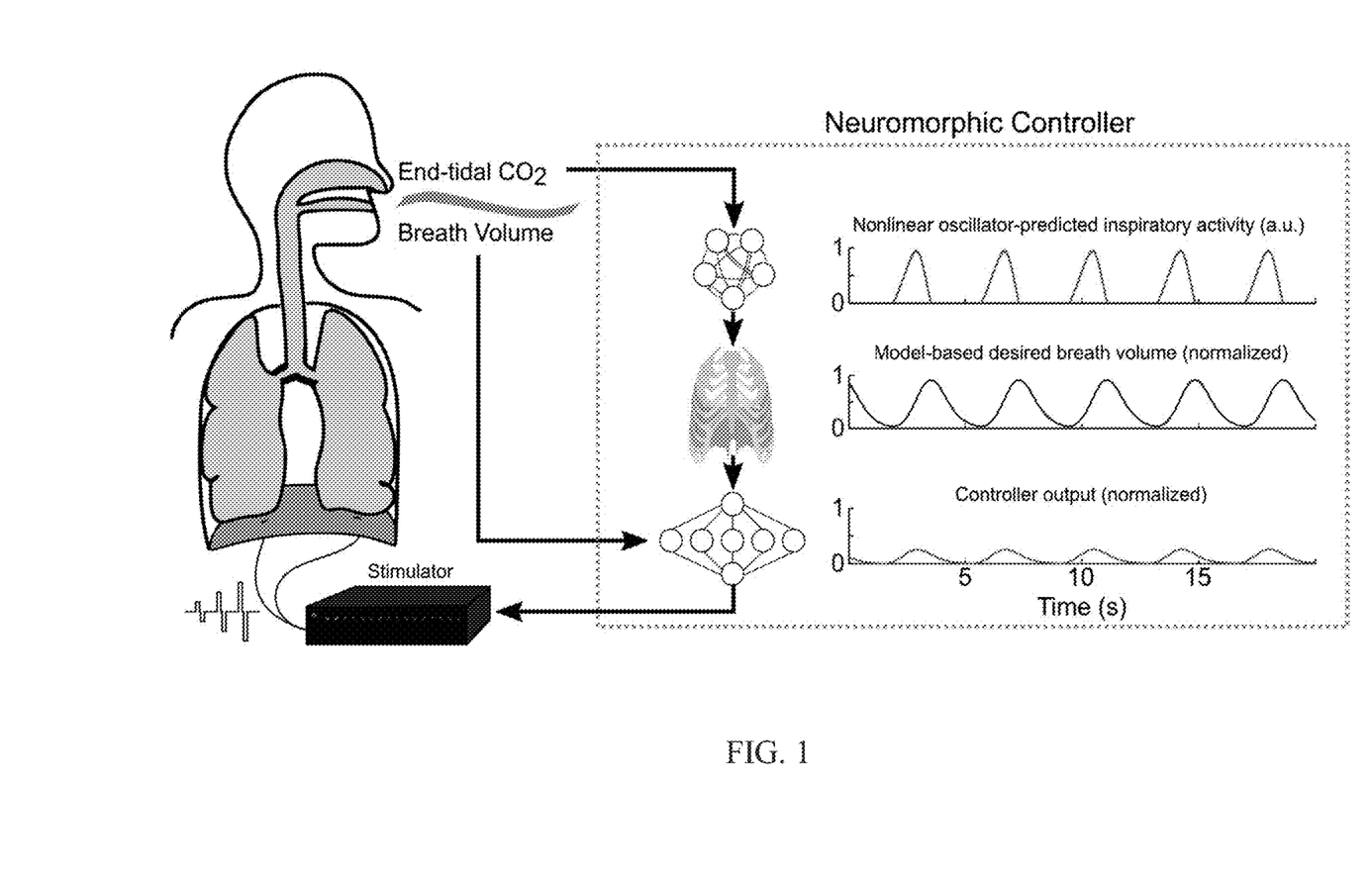
FIG. 1 shows a conceptual view of an adaptive neuromorphic closed-loop control system for respiratory pacing, according to an embodiment of the subject invention.

FIG. 1 shows a conceptual view of an adaptive neuromorphic closed-loop control system for respiratory pacing, according to an embodiment of the subject invention. Referring to FIG. 1, the adaptive controller can use measurements of etCO$_2$ of a subject to predict, through a model-based approach, an adequate ventilatory response for the subject. The controller can then use measured breath volume of the subject to autonomously tune pacing parameters such that the ventilatory pattern evoked by diaphragmatic stimulation matches the desired ventilatory pattern. This two-stage closed-loop approach can allow for a respiratory pacing system that can adapt, on a breath-by-breath basis, to continuously adjust pacing to evoke an adequate ventilatory response.

Figure 2:
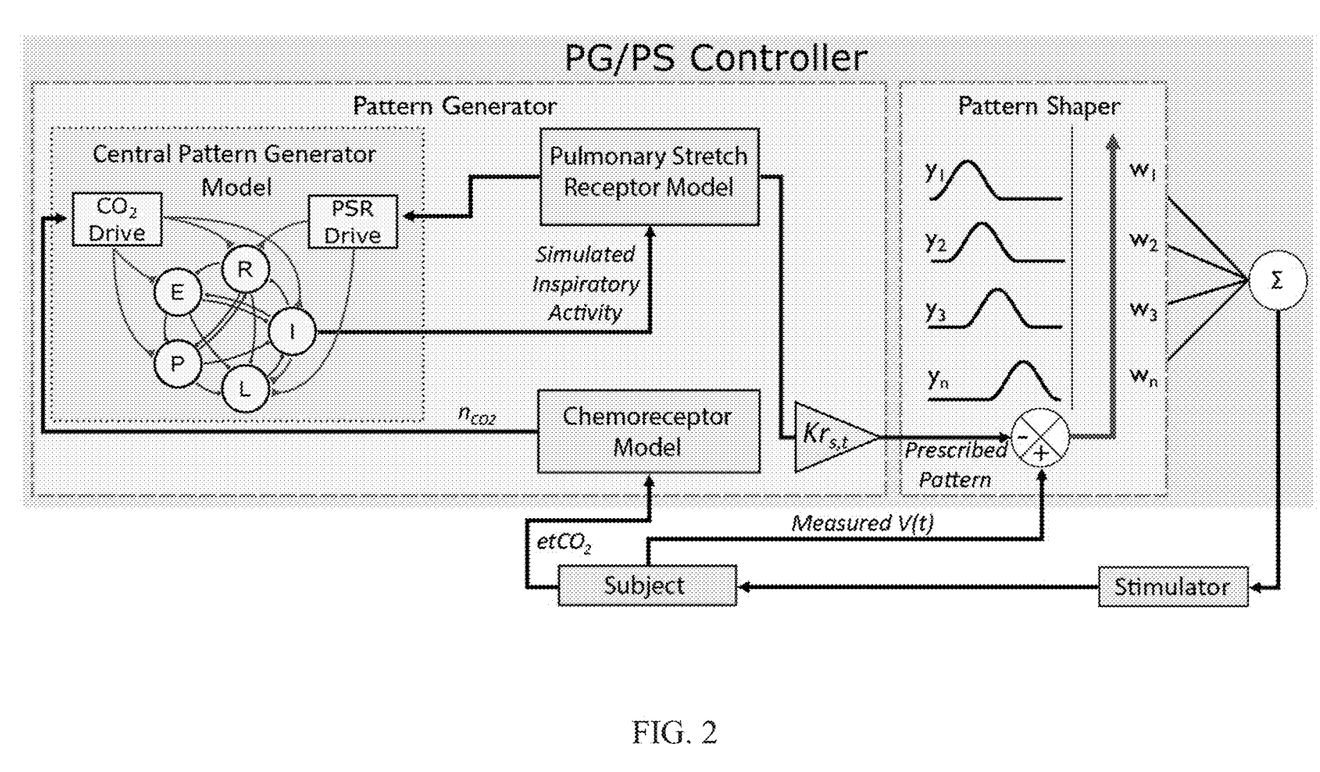
FIG. 2 shows a block diagram of a pattern generator (PG)/pattern shaper (PS) adaptive controller, according to an embodiment of the subject invention.

FIG. 2 shows a block diagram of a PG/PS adaptive controller, according to an embodiment of the subject invention. Referring to FIG. 2, the PG can be used to prescribe a ventilatory pattern for a subject, and the PS can be used to determine the stimulation required for pacing of the diaphragm to attain the prescribed pattern. The PG can integrate a computational model of the respiratory central pattern generator (rCPG) (see Botros et al., Neural network implementation of a three-phase model of respiratory rhythm generation, Biol. Cybern. 63, 143-153 (1990); which is hereby incorporated by reference herein in its entirety), a pulmonary stretch receptor (PSR) model, and/or a $CO_2$ chemoreceptor model to generate a ventilatory response, which can be scaled in amplitude by a factor ($Kr_s$) and in time by a nominal factor ($Kr_t$) to prescribe a breath volume profile to be elicited. The PS can derive a volume-based error measure used to continuously modulate network weights, which can ultimately help define the amplitude of the stimulation delivered to the diaphragm of the subject. Changes in partial pressure of arterial $CO_2$ ($PaCO_2$) due to changes in ventilation can be reflected in changes in $etCO_2$. The chemoreceptor model can convert $etCO_2$ to neural $CO_2$ drive, which can modulate activity within the rCPG, generating a new inspiratory pattern and closing the control loop. Breath volume at time t is represented as V(t); partial pressure of arterial $CO_2$ is represented as $PaCO_2$; end-tidal $CO_2$ is represented as $etCO_2$; partial pressure of venous $CO_2$ is represented as $PvCO_2$; neural $CO_2$ drive from chemoreceptor is represented as $nCO_2$; $Kr_s$ is the amplitude scaling factor; and $Kr_t$ is the duration scaling factor.

Figure 3:
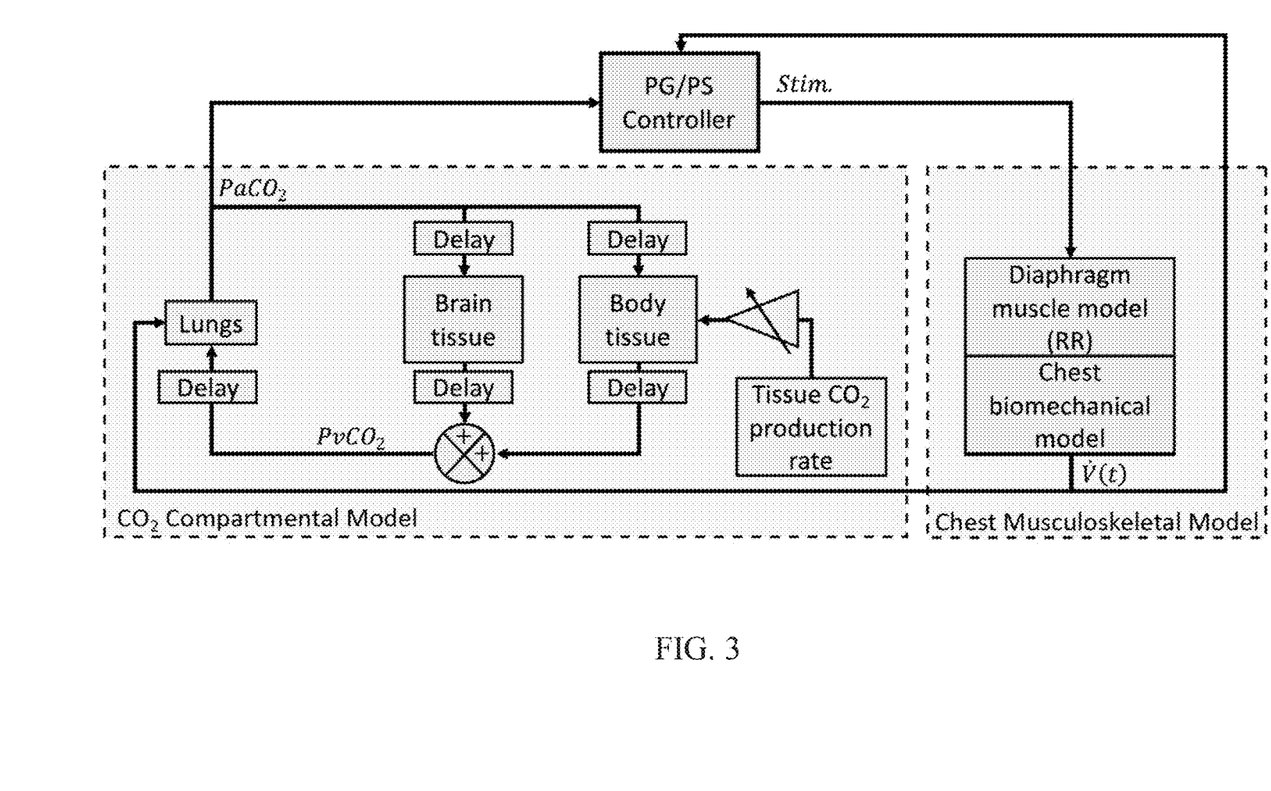
FIG. 3 shows a block diagram of a computational testbed, according to an embodiment of the subject invention, used to assess in silico the PG/PS controller of FIG. 2.

FIG. 3 shows a block diagram of a computational testbed, according to an embodiment of the subject invention, used to assess in silico the PG/PS controller of FIG. 2. Referring to FIG. 3, a chest musculoskeletal model with reverse recruitment (RR) dynamics and a $CO_2$ compartmental model can be linked with the PG/PS controller. The ventilation, V(t), elicited by the chest musculoskeletal model can drive changes in $PaCO_2$ in the compartmental model of $CO_2$ dynamics. $PaCO_2$ can be sampled by the controller, which can then drive force generated by the muscle model. Changes in the gain of $CO_2$ production rate within the tissue (labeled "Tissue $CO_2$ production rate" in FIG. 3) can be used to simulate changes in metabolic demand. The eventual change in $PaCO_2$ can be used to assess the controller's ability to maintain normocapnia despite changes in metabolic demand that may result from increased exercise or other changes in metabolic activity. Model parameters and values can be obtained, for example, from literature.

Related art technology for controlling a "diaphragm pacer" is not capable of automated, real-time adaptations to patient needs. Rather, the pacer is set manually and stimulation parameters remain fixed until further adjustment by a medical practitioner. In health, alveolar ventilation is exquisitely regulated such that arterial levels of carbon dioxide are maintained around a tight "set point" of approximately 40 mmHg, such that a 1 mmHg change in arterial $CO_2$ can cause a significant change in breathing. This tight matching of breathing with $CO_2$ delivery is required to maintain acid/base homeostasis and is a fundamental aspect of ventilatory control in humans. Embodiments of the subject invention provide closed-loop diaphragm-pacing controllers that mimic the endogenous biological controller by responding to changes in metabolic demand with appropriate changes in ventilation, but without the need for manual manipulation of pacing parameters. The PG/PS controller can also be used under other circumstances that require respiratory assistance or when weaning from mechanical ventilation.

In patients with acute respiratory distress syndrome (ARDS), as seen for example with COVID-19, the lung compliance decreases due to fibrosis after alveolar-capillary damage. In such cases, adaptive pacing can deliver stimulation to assist the patient's intrinsic breathing. Additionally, the controller can continuously monitor $etCO_2$ and control ventilation to ensure that normocapnia is maintained regardless of changes in lung biomechanics. The PG/PS controller and temporary phrenic stimulation technology of embodiments can be integrated with an oxygen supply with adequate positive end expiratory pressure (to minimize alveolar collapse). This integrated approach may allow patients to breathe in an assisted-as-needed manner, avoid or reduce volutrauma/barotrauma and diaphragm atrophy, decrease or avoid the weaning period, and/or require less supervision by trained professionals.

Closed-loop adaptive controllers with neuromorphic architecture, according to embodiments of the subject invention, have the potential for clinical impact on individuals who require respiratory assistance by providing automated real-time selection of stimulation parameter settings to achieve suitable ventilation in response to changes in metabolic demand. The controller can allow the user/subject to engage in activities that elevate metabolic demand without risking hypoventilation (or while significantly decreasing the risk of hypoventilation).

A neuromorphic closed-loop adaptive controller of an embodiment of the subject invention was developed and evaluated first in silico and then in vivo using two animal models of hypoventilation (see the Examples presented herein). The controller automatically adapts to changes in expired $etCO_2$ levels and prescribes a ventilatory pattern on a breath-by-breath basis. The etCO2 is easily measured and may be used as a practical, albeit not perfect, alternative for direct arterial $CO_2$ measurement. The controller produces, in real-time, the prescribed ventilatory pattern by modulating diaphragm muscle stimulation. The approach enables generation of the desired dynamic volume profile within a given breath, thereby preventing or inhibiting respiratory acidosis or alkalosis if metabolic (and thus respiratory) demand changes. This biologically-inspired adaptive closed-loop respiratory pacing control scheme (see FIG. 1) is the first ever for management of arterial $CO_2$ during respiratory pacing. Closed-loop control of $etCO_2$, and by extension arterial $CO_2$, in people with ventilatory impairments can alleviate concerns about inadequate ventilation during low-intensity activities, as well as allow ambulatory and/or partially ambulatory patients to lead a more active lifestyle without risk of hypoventilation (or with substantially reduced risk of hypoventilation), thereby leading to improvements in health and quality of life.

In many embodiments, the PG/PS controller design is based on the biological ventilatory control scheme, where the PG generates a ventilatory pattern and the PS adapts stimulation parameters to evoke a prescribed ventilatory pattern. The PG module can include a triphasic oscillatory network to mimic the behavior of the rCPG (see Botros et al. (1990), supra.). This rCPG model uses a $CO_2$-based input to determine an appropriate inspiratory duration, which is then converted into a breath volume profile through the use of a chest biomechanical model. The volume profile and cycle duration are scaled and passed on to the PS to serve as the prescribed ventilatory pattern.

The rCPG network model used can include five interconnected neuronal populations. The activity of each of these populations can be maximal at different phases of the respiratory cycle, these being early-inspiratory, inspiratory, late-inspiratory, post-inspiratory, and expiratory. These populations can receive mostly inhibitory input from each other as well as from other sources, such as chemoreceptors and pulmonary stretch receptors. The equations for this oscillating respiratory network are, $$\frac{dI}{dt} = -a_I I - W_{EI}S(E) - W_{PI}S(P) - W_{LI}S(L) + W_{II}S(I) + n_{CO_2}B_I \quad (1)$$

$$\frac{dL}{dt} = -a_L L + W_{IL}S(I) - W_{EL}S(E) - W_{RL}S(R) + W_{LL}S(L) + B_L + W_{vL}v \quad (2)$$

$$\frac{dP}{dt} = -a_P P - W_{EP}S(E) - W_{RP}S(R) + W_{PP}S(P) + n_{CO_2}B_P \quad (3)$$

$$\frac{dE}{dt} = -a_E E - W_{IE}S(I) - W_{RE}S(R) - W_{EE}S(E) + n_{co2}B_E \quad (4)$$

$$\frac{dR}{dt} = -a_R R - W_{IR}S(I) - W_{PR}S(P) + W_{RR}S(R) + n_{CO_2}B_R + W_{vR}v \quad (5)$$

where I, L, P, E, and R represent the inspiratory, late-inspiratory, post-inspiratory, expiratory, and early inspiratory neuronal populations, respectively, while v represents the input from the vagus nerve, which carries pulmonary stretch receptor information. The self-decay term denoting the rate of decay is defined by $a_i$, where I is the respective neuronal population. This term allows for silencing of the i-population when no input is present. $W_{ji}$ refers to the gain of the signal, or weight, of the j neuron to the i neuron, whereas $W_{ii}$ is the self-activation factor. $B_i$ refers to the weight of the chemoreceptor signal, $n_{CO_2}$, which is considered to change linearly with $PaCO_2$. In order to convert firing frequency of the neuronal population to population activity, a sigmoid function, S, is used:

$$S(X) = K \cdot \alpha + (1 - K) \cdot \beta \quad (6)$$

$$\alpha(X) = \begin{cases} \min(X, 4) & \geq 0 \\ 0 & < 0 \end{cases} \quad (7)$$

$$\beta(X) = \frac{4}{1 + e^{-1.75 \cdot (X-2)}} \quad (8)$$

where X is the firing frequency and K is a constant that determines the steepness of the function.

The chemoreceptor input, $n_{CO_2}$, is given as a bounded linear function of $PaCO_2$:

$$n_{CO_2} = \begin{cases} P_aCO_2 > 35 & n_{CO_2} = 0.2 \\ 45 < P_a(CO)_2 < 35 & n_{CO_2} = (PaCO_2 \cdot 0.072) - 2.32 \\ P_a(CO)_2 < 45 & n_{CO_2} = 1.72 \end{cases} \quad (9)$$

The limits of 0.2 and 1.72 were set as a result of a set of preliminary simulations performed on the rCPG model to obtain the minimum and maximum $n_{CO_2}$ values at which a physiologically relevant response was obtained. The linear function constants were set so that a linear response between a $PaCO_2$ of 35 to 45 mmHg is maintained.

In order to reduce the effect of transient events, an exponential moving average (EMA) of the peak $PaCO_2$ with a time constant, τ, of 8 seconds (s) was utilized. This was determined through simulations, as discussed in the examples presented herein.

In order to represent the pulmonary stretch receptor input v, which contributes to the oscillatory behavior of the rCPG, a basic model to represent pulmonary expansion is used, $$\frac{dv}{dt} = -K_1 \cdot v(t) + K_2 \cdot S(I) \quad (10)$$

where K1 and K2 are constants set such that v increases during inspiration but decays as v(t) increases, reflecting the Hering-Breuer reflex. When this model is paired with the previously described rCPG equations and chemoreceptor model, rhythmogenesis occurred, producing a ventilatory response to $PaCO_2$ similar to that observed in mammals. Given that this basic model creates a pattern that represents pulmonary stretch, it can thus be used to derive a breath volume profile.

The output of the inspiratory pool of the rCPG was half-wave rectified and processed through the pulmonary stretch receptor model. The pulmonary stretch receptor output was then scaled in amplitude to match the tidal volume expected for the weight of each rat. The range of the cycle duration of the rCPG output was also scaled in time to match the range of breath durations observed in rats under eupneic (see Whitehead et al., Pulmonary Function in Normal Rats, http://www.stormingmedia.us/56/5687/A568763.html (1999); and Cragg et al., Interaction of hypoxia and hypercapnia on ventilation, tidal volume and respiratory frequency in the anaesthetized rat, J. Physiol. 341, 477-93 (1983).; both of which are hereby incorporated by reference herein in their entireties) to hypercapnic (see Whitehead et al, supra.; and Molkov et al., A closed-loop model of the respiratory system: Focus on hypercapnia and active expiration, PLoS One 9, e109894 (2014); which is hereby incorporated by reference herein in its entirety) conditions. This scaled ventilatory pattern then provided, on a breath-by-breath basis, a prescribed trajectory for the PS module to follow. In the examples presented herein, if $etCO_2$ information was unavailable (e.g., first breath of pacing), the controller worked under the assumption that the $etCO_2$ input is 36 mmHg.

The PS module for respiratory control was as in Siu et al. (see Siu et al., Restoring Ventilatory Control Using an Adaptive Bioelectronic System, J. Neurotrauma 36, 3363-3377 (2019); which is hereby incorporated by reference herein in its entirety). The PS module aims to determine adequate stimulation parameters to elicit a specified breath volume profile. In Siu et al. (supra.), this prescribed profile was preset based on baseline breath volumes and profiles for each rat; here, the prescribed profile was generated by the PG module. Briefly, the PS includes a single-layered neural network with time-shifted activation profiles. The output of the controller z, is a value from 0 to 1, which is multiplied by the maximum allowed current amplitude. This is given by $$z(t) = \sum_{j=1}^{n_a} w_j(t) y_j(t) \quad (11)$$

The output is defined by the summation of the weighted output ($y_j$) of all active neurons, $n_a$. Neuronal weights for each neuron j are given by $w_j$. The PS uses a comparator to define the error at any time t, e(t), between the prescribed volume trajectory defined by the PG module and the measured volume profile. The change in weight $\Delta w_j$, for all neurons at time t is defined by $$\Delta w_j(t) = \eta e(t) \sum_{k_p=1}^{n_p} \frac{1}{n_p} y_j(t - k_p T) \quad (12)$$

where $\eta$ is the learning rate, $n_p$ is the number of past activations over which the error will be time averaged to account for delays in activation, and $y_j(t-k_p T)$ is the output of neuron j at previous times. Hence, the error at time t affects all neurons that have been recently active; the amount of change is proportional to its activity over the specified window ($n_p T$).

The neural network contains a maximum of 72 neurons time shifted every 0.014 s to span a duration of 1.05 s. In order to account for changes in breath cycle duration, the network is re-organized by excluding a certain number of neurons of the network at the start of every breath to match the new prescribed cycle duration. Thus, as $PaCO_2$ increases and the PG module prescribes a ventilatory pattern with reduced cycle duration, neurons with zeroed weights (an indication of no influence on stimulation) are excluded. This shortens the cycle such that the updated cycle duration closely matches that of the shortened prescribed breath duration. Once $PaCO_2$ decreases and the PG module prescribes an increase in breath cycle duration, these neurons are included to prolong the cycle duration. In this manner, the PS is able to work in concert with the PG module to evoke the prescribed ventilatory pattern.

Figure 7:
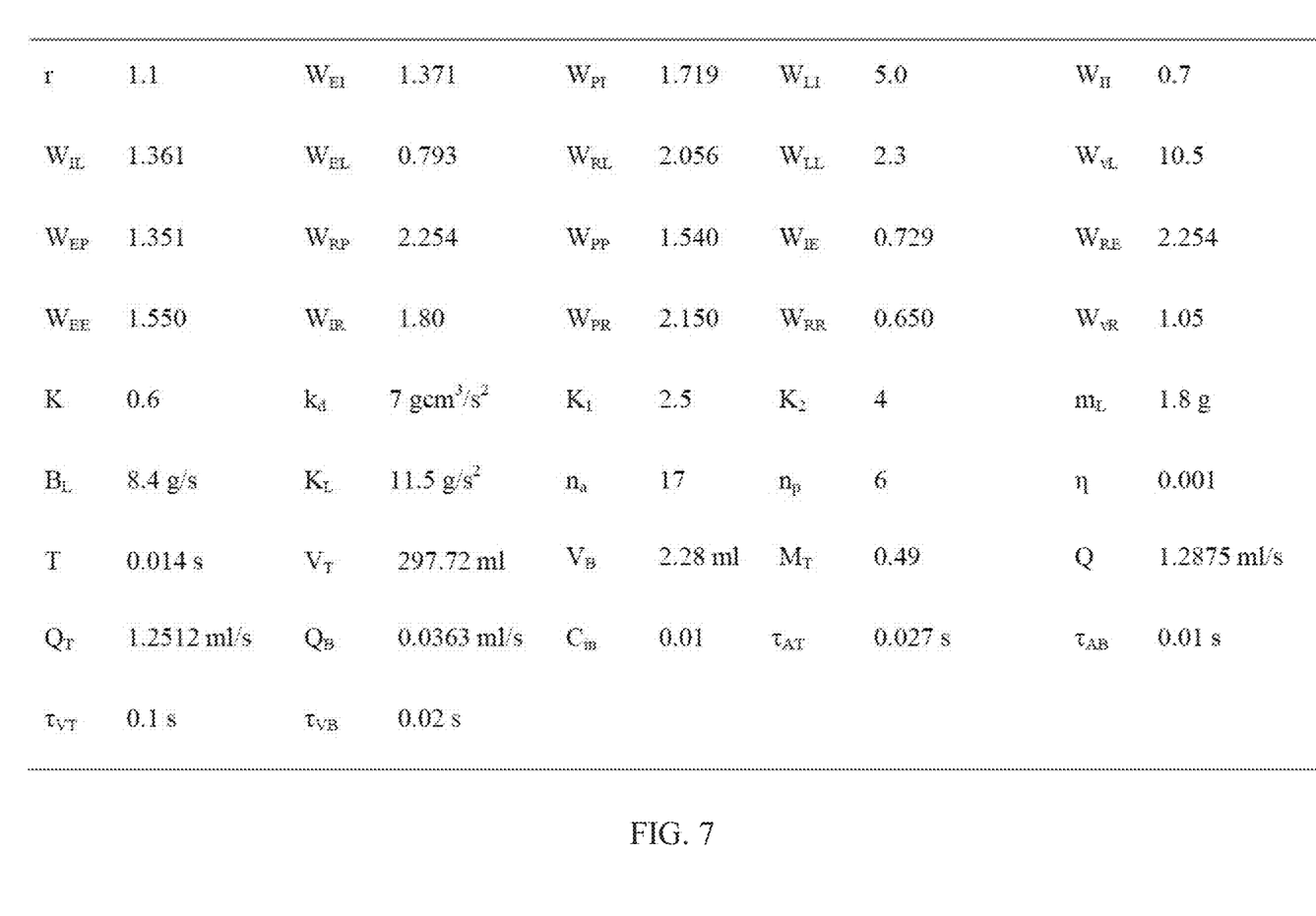
FIG. 7 shows a table of constants for a PG/PS controller, according to an embodiment of the subject invention that was programmed and implemented in LabVIEW (National Instruments, Austin, Tex.) for both in vivo and in silico studies.

The PG/PS controller was programmed and implemented in LabVIEW (National Instruments, Austin, Tex.) for both in vivo and in silico studies. All controller constants are shown in FIG. 7. In the animal studies in Examples 2 and 3, the controller output to the stimulator was scaled such that the maximum allowed current amplitude was four times the twitch threshold.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

MATERIALS AND METHODS

Animal use was approved by the Institutional Animal Care and Use Committee of Florida International University. All experiments were performed in accordance with relevant guidelines and regulations. Experiments were completed in anesthetized, spontaneously breathing, adult, male Sprague-Dawley rats with an intact spinal cord (Group 1, n=7, weight of 411±91 grams (g), age of 3.6±0.9 months) or with a left cervical (C2) spinal cord hemisection (Group 2, n=6, weight of 390±80 g, age of 3.4±0.8 months). Rats were anesthetized with urethane (1.5 g/kg, s.c.) and supplemental isoflurane (0.2-1.5% in 100% $O_2$). Body temperature and plane of anesthesia were monitored throughout the experiment. After tracheostomy, airflow was measured using a pneumotachometer (PTM Type HSE-73-0980, Harvard Apparatus, Holliston, Mass.) and integrated (0.2 seconds (s) time constant; PI-1000, CWE Inc, Ardmore, Pa.) to provide breath volume. End-tidal $CO_2$ ($etCO_2$) was monitored (CapStar-100, CWE Inc., Ardmore, Pa.) as a proxy for partial arterial pressure of $CO_2$ ($PaCO_2$). Hemi-diaphragmatic electromyograms ipsilateral to the spinal hemisection were used to confirm functional hemiparesis. At experiment termination, the spinal cord tissue was harvested and later histologically assessed for hemisection verification.

Intramuscularly implanted single-stranded, stainless steel electrodes (SS-304, 44 AWG, AM-Systems, Carlsborg, Pa.) were used to stimulate each hemidiaphragm. A stimulator (FNS-16, CWE Inc., Ardmore Pa.) delivered biphasic cathodic-first current pulses (200 microseconds per phase (μs/phase), 80 μs inter-phase interval at 72 Hertz (Hz)) at a variable current amplitude determined by the controller at a maximum of four times the twitch threshold.

A goal was to assess whether the PG/PS controller could autonomously control breath volume and respiratory rate to restore normocapnia. Hypoventilation, with associated hypercapnia, was induced by either delivery of additional isoflurane, a known respiratory depressant, or via spinal cord injury (SCI). An elevation of $etCO_2$ served as a marker of hypoventilation. In the respiratory depressed group, once an $etCO_2$ value of 50 millimeters of mercury (mmHg) or more was reached, the pacing trial was initiated. In the SCI group, baseline ventilatory recordings were collected after electrode implantation but prior to SCI. A period of at least 30 minutes (min) served to stabilize the immediate effects of the injury. After a 30 min stabilization period and when $etCO_2$ exceeded 50 mmHg, the pacing trial was initiated.

Trials included 60 s of spontaneous breathing after which the PG/PS was enabled; pacing was maintained for at least 900 s without intervention. On cessation of pacing, a 30 min rest period ensued. If $etCO_2$ exceeded 50 mmHg during rest, mechanical ventilatory support was provided to reduce etCO$_2$ below 50 mmHg. In all trials, the desired ventilatory pattern was determined by the PG module of the controller based on etCO$_2$ feedback and animal body weight as described above. PG/PS controller-based pacing was considered successful if etCO$_2$ was reduced to within normocapnic range (36±7 mmHg) during stimulation.

The performance of the PG/PS controller was evaluated by measuring ventilation. An "adequate ventilation" was determined by whether or not etCO$_2$ values returned towards normocapnic levels and if normocapnia was maintained throughout the trial. The ability of the PG/PS controller to maintain the desired ventilatory pattern was assessed by measuring the inspiratory root mean square error (iRMSE), which provides a measure of the error between the elicited volume and the desired volume profile.

The first 20 cycles of iRMSE after entrainment and the last 20 cycles of the trial were compared to assess whether controller performance declined over time. The controller's ability to achieve normocapnia was calculated as the average decrease in etCO$_2$ from the 20 breath cycles obtained after pacing was initiated and entrainment had occurred to the last 20 cycles of the 1000 cycle trial.

A general linear mixed model (see Cnaan et al., Using the general linear mixed model to analyse unbalanced repeated measures and longitudinal data, Stat. Med. 16, 2349-2380 (1997); which is hereby incorporated by reference herein in its entirety) was used to assess the effect of PG/PS controlled pacing on PaCO$_2$. Fixed effects included trial number and condition (prior to pacing and after pacing) and random intercept effects of both trial number and measurement occasion (last 20 breath measurements within each trial). All descriptive statistics are given in the form of mean f standard deviation. The generalized linear mixed model was performed using SAS 9.4 (SAS Institute Inc., Cary, N.C.).

The neuromorphic controller shares some characteristics with a PG/PS scheme for lower limb control (Abbas et al., Experimental evaluation of an adaptive feedforward controller for use in functional neuromuscular stimulation systems, IEEE Trans. Rehabil. Eng. 5, 12-22 (1997); and Fairchild et al., Repetitive hindlimb movement using intermittent adaptive neuromuscular electrical stimulation in an incomplete spinal cord injury rodent model, Exp. Neurol. 223, 623-633 (2010); both of which are hereby incorporated by reference herein in their entireties). A mathematical model of the respiratory central pattern generator (rCPG) served as the basis for respiratory rhythmogenesis (see FIG. 2). An adaptive PG module integrated the rCPG with a chemoreceptor model and a pulmonary stretch receptor model to prescribe an appropriate ventilatory pattern in response to changes in PaCO$_2$ (in silico) or etCO$_2$ (in vivo) on a breath-by-breath basis. The PG module was coupled to an adaptive PS module, which leveraged an adaptive neural network to determine stimulation parameters for diaphragmatic pacing to evoke the PG-prescribed ventilatory pattern. The model is described in detail above, and controller and model parameter values are shown in FIG. 7.

The desired breath volume profile is generated automatically by the PG module. The PG module utilizes a triphasic oscillatory network of five interconnected neuronal pools of respiratory neurons to mimic the behavior of the rCPG. For every breath, it uses model-based chemoreceptor drive and model-based pulmonary stretch receptor feedback drive to determine an appropriate inspiratory duration for the next breath. The chemoreceptor drive to the PG is a bounded linear function of PaCO$_2$ in silico (35-45 mmHg) and etCO$_2$ (30-45 mmHg) in vivo. These bounds limit the maximum breath amplitude produced by the PG module, thus guarding against volutrauma. In order to minimize unwanted ventilatory responses to spurious changes in PaCO$_2$ in silico or etCO$_2$ in vivo, an exponential moving average of the peak PaCO$_2$/etCO$_2$ was utilized (time constant=8 s). The output from the pulmonary stretch receptor model was used as an additional drive for rhythmogenesis, resulting in a ventilatory response to PaCO$_2$/etCO$_2$ that matched that observed in mammals.

The output of the inspiratory pool of the rCPG was half-wave rectified and processed through the pulmonary stretch receptor model. The pulmonary stretch receptor output was then scaled in amplitude to match the tidal volume expected for the weight of each rat. This output was also scaled in time to match endogenous respiratory rates during eupneic and hypercapnic conditions. This ventilatory pattern was obtained on a breath-by-breath basis, serving as the prescribed trajectory for the PS module to follow. In the experiments, if etCO$_2$ information was unavailable (e.g., first breath of pacing), the controller worked under the assumption that the etCO$_2$ input was 36 mmHg.

The PS module, a neural network with 72 neurons time-shifted every 0.014 s, aims to determine adequate stimulation parameters to elicit a specified breath volume profile. This prescribed profile now also varies in cycle duration. Hence, to account for changes in the prescribed breath cycle duration, neurons in the network were silenced or reactivated at the start of every breath to modulate the pacing cycle duration. In this manner, the PS was able to work in concert with the PG module to evoke the prescribed ventilatory pattern.

The PG/PS controller was programmed and implemented in LabVIEW (National Instruments, Austin, Tex.). In animal studies, the controller output to the stimulator was scaled such that the maximum stimulator output was four times the twitch threshold. The controller was assessed in silico to test functionality prior to in vivo studies. Its ability to respond to changing metabolic conditions was assessed in vivo in two animal models of hypoventilation-induced hypercapnia.

The PG/PS controller was developed and validated computationally prior to in vivo assessment. A comprehensive computational model containing biomechanical, muscular, and CO$_2$ dynamics was developed based on a model for rat musculoskeletal dynamics (see Siu et al., supra.) A computational model for CO$_2$ generation in humans (see also Topor et al., Model based analysis of sleep disordered breathing in congestive heart failure, Respir. Physiol. Neurobiol. 155, 82-92 (2007); Lessard, Basic feedback controls in biomedicine, Synthesis Lectures on Biomedical Engineering vol. 4 (Morgan & Claypool, 2009); and Milhorn, The respiratory system, in Application of control theory to physiological systems 230-254 (WB Saunders, 1966); all of which are hereby incorporated by reference herein in their entireties) was adapted and scaled to match rat normative values found in literature (see Whitehead et al., supra.; and Molkov et al., supra.) and integrated with the biomechanical model. The organization of these models and their integration with the adaptive PG/PS controller is illustrated in FIG. 3. A list of constants and variables used for these models is shown in FIG. 7.

The model describing CO$_2$ dynamics used is that of a CO$_2$ compartmental model containing a general body tissue compartment, a brain compartment, and a lung compartment with appropriate CO$_2$ transport delays (see also see Molkov et al., supra.). The body tissue and brain compartments produce CO$_2$ based on compartment volumes and a rate of CO$_2$ production as described below for the body tissue compartment.

$$V_T \frac{dC_T}{dt} = \dot{M}_T + \dot{Q}_T(C_a + C_T) \quad (13)$$

Referring to Equation (13), the concentration of $CO_2$ of the compartment $C_T$, is given by volume of the compartment $V_T$, metabolic rate of the compartment $\dot{M}_T$, given as $CO_2$ production rate, perfusion through the tissue compartment $\dot{Q}_T$, and arterial $CO_2$ concentration from the arterioles to the compartment tissue $C_a$. An identical equation is used to determine $CO_2$ concentration derived from the brain tissue compartment by replacing volume, metabolic rate, perfusion rate with the respective values for the brain tissue. The total venous $CO_2$ concentration $C_V$, is given by the concentration of venous $CO_2$ coming from the brain and body tissue compartments $C_{vB}$ and $C_{vT}$, respectively, and their respective perfusion rates.

$$\frac{dC_V}{dt} = \dot{Q}_B C_{vB} + \dot{Q}_T C_{vT} \quad (14)$$

The concentration of $CO_2$ within the alveoli is given using the lung compartment equation defined as $$\frac{dVC_a}{dt} = \begin{cases} \dot{Q}(C_V - C_a) + \dot{V}C_{in} & \dot{V} \geq 0 \\ \dot{Q}(C_V - C_a) + \dot{V}C_a & \dot{V} < 0 \end{cases} \quad (15)$$

where arterial $CO_2$ concentration is given by lung volume V, venous $CO_2$ concentration, total perfusion $\dot{Q}$, inspired $CO_2$ concentration $C_{in}$, and ventilation $\dot{V}$.

The time constant of the EMA was selected based on simulations to assess the controller's response to two different physiological scenarios: a sudden increase in metabolic demand; and apnea. The sudden increase in metabolic demand was modeled by increasing $CO_2$ production in the tissue by 50% at 180 s after pacing initiation. Apnea was simulated by setting diaphragm activation to zero for one cycle 300 s after pacing initiation. Time constants of 1 s, 2 s, 4 s, 6 s, 8 s, 10 s, 15 s, 20 s, 25 s, and 30 s were used for the EMA. The controller's response was assessed via the root mean square error (RMSE) between the measured $PaCO_2$ response and an idealized $CO_2$ response from 5 s prior to the increase in $CO_2$ rate production to 60 s after the apneic event. The standard deviation in RMSE was used to characterize stability after perturbation while the maximum RMSE was used to assess magnitude of the overshoot caused by the controller after the perturbation.

In order to assess the controller's ability to control ventilation reliably in response to changes in $PaCO_2$ in a closed-loop manner, simulations were performed with varying rates of $CO_2$ production in the tissue. The value for $CO_2$ production rate was modified to be 10%-200% of baseline $CO_2$ production after 180 s to simulate changes in respiratory demand due to metabolic activity. The ability to achieve normocapnia by the end of the trial was used to assess the controller's performance. The adaptive PG/PS controller was compared to a version of the controller with a fixed PG pattern that did not have the ability to directly respond to $PaCO_2$, but with an adaptive PS that attempted to match the breath volume profile.

In computational (in silico) trials, the PG/PS controller's ability to determine a prescribed ventilatory output was assessed by observing the change in prescribed tidal volume and prescribed breath duration with respect to the model's $PaCO_2$ output and comparing this trend to the expected ventilatory response to hypercapnia found in literature.

Example 1—Computational Study to Confirm Ability to Respond to Metabolic Demand

Figures 4A, 4B, 4C:
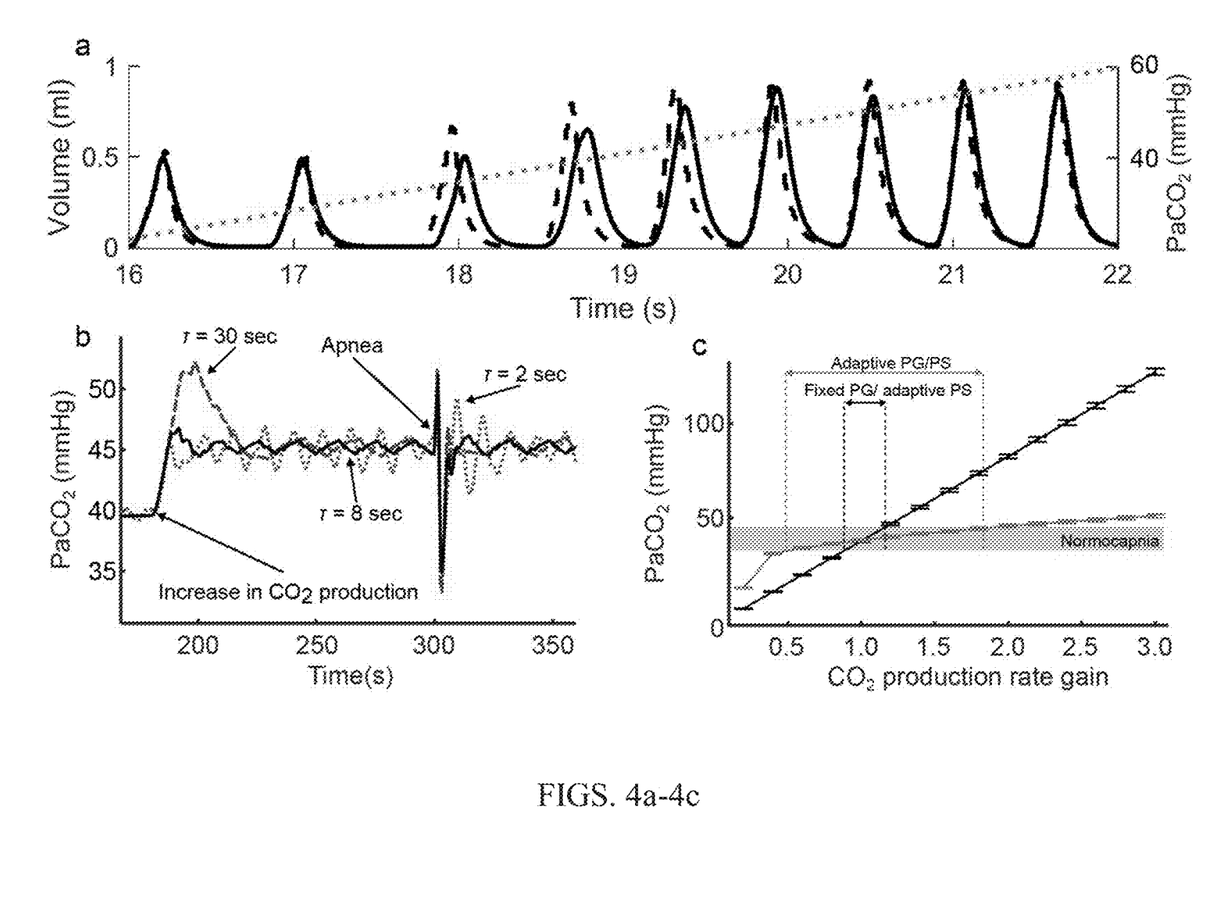
FIG. 4a shows a plot of volume (in milliliters (ml); left y-axis) and partial arterial pressure of carbon dioxide (PaCO$_2$; in millimeters of mercury (mmHg); right y-axis) versus time (in seconds (s)), illustrating adaptive PG, adaptive PS response to a ramping increase in PaCO$_2$ values. The PG module generated a prescribed ventilatory profile (dashed curved lines) in response to a controlled increase in PaCO$_2$ levels (dashed straight line). The PS module responded by adapting stimulation to elicit a breath volume (solid curved lines) matching that of the pattern dictated by the PG.
FIG. 4b shows a plot of PaCO$_2$ (in mmHg) versus time (in s), illustrating an evaluation of the adaptive PG/PS response to PaCO$_2$ under chemo-transducer time constants of 2 sec (dotted (blue) curve), 8 sec (solid (black) curve), and 30 sec (dashed (red) curve). A time constant of 8 sec provided the best stability and robustness to perturbations.
FIG. 4c shows a plot of PaCO$_2$ (in mmHg) versus CO$_2$ production rate gain, illustrating a comparison between the ability of a fixed PG/adaptive PS controller (solid (black) line with the higher value CO$_2$ production rate gain of 3.0) and an adaptive PG/PS controller (solid (gray) line with the lower value CO$_2$ production rate gain of 3.0) to maintain normocapnia. The adaptive PG/PS controller can maintain normocapnia across a wider range of the baseline CO$_2$ production rate than the fixed PG/adaptive PS.

Computational studies showed that the controller could compute and produce a ventilatory pattern capable of restoring normocapnia when provided with a wide range of $PaCO_2$ values. FIG. 4a shows that the controller responds to an increase in $PaCO_2$ by increasing tidal volume and decreasing cycle period.

FIG. 4b illustrates the controller's response to sudden changes in $PaCO_2$ under time constant values of 2 s, 8 s, and 30 s. After a 50% increase in $CO_2$ production, low values of T led to a fast response but unstable oscillatory behavior long after the perturbation. Larger values achieved stability but caused a significant overshoot in $PaCO_2$ after apnea. Overall, a T of 8 s led to a small overshoot with minimal underdamping as represented by the lowest $PaCO_2$ root mean square error (RMSE) among all other T values.

Comparison between a version of the controller with a fixed-PG (non-responsive to changes in $PaCO_2$) and a version with an adaptive PG (closed-loop $PaCO_2$ control) demonstrated that the fixed-PG controller was able to maintain normocapnia within 89% to 115% of the baseline $CO_2$ production rate, while the adaptive PG controller was able to achieve normocapnia within a larger range of 52% to 200% of the baseline $CO_2$ production rate, as seen in FIG. 4c.

Example 2—Restoring Normocapnia after Anesthesia-Induced Hypoventilation

Figures 5A, 5B, 5C, 5D, 5E:
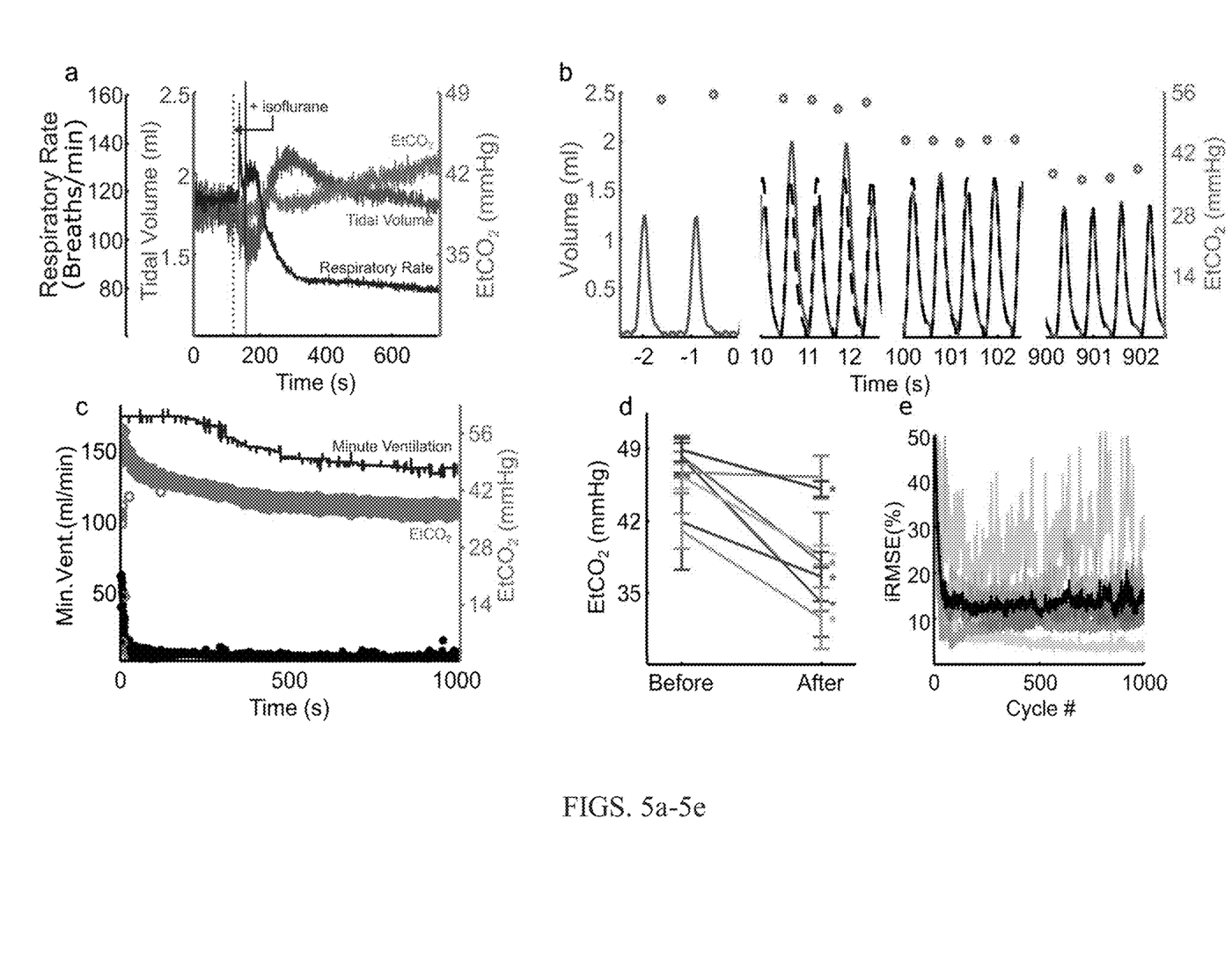
FIG. 5a shows a plot of respiratory rate (in breaths per minute (breaths/min); left y-axis) and etCO$_2$ (in mmHg; right y-axis) versus time (in s), illustrating that supplemental isoflurane (+1.5%, 100% O$_2$) caused hypoventilation mainly via a decrease in respiratory rate ((black) curve labeled as "respiratory rate"), which led to an increase in etCO$_2$ ((orange) curve labeled as "EtCO$_2$").
FIG. 5b shows a plot of volume (in ml; left y-axis) and etCO$_2$ (in mmHg; right y-axis) versus time (in s), illustrating ventilatory pattern prior to controller initiation (0 sec), following ventilatory entrainment (100 sec), and 900 sec after controller initiation. The adaptive PG/PS was able to respond to the elevated peak etCO$_2$ ((orange) circles) by eliciting a hyperventilatory pattern ((black) dashed line) and adapting stimulation to match the measured volume ((blue) solid line) to the desired pattern. After 900 sec, etCO$_2$ was within acceptable levels and thus the ventilatory pattern elicited showed a decreased tidal volume and respiratory rate.
FIG. 5c shows a plot of minute ventilation (in milliliters per minute (ml/min); left y-axis) and etCO$_2$ (in mmHg; right y-axis) versus time (in s), illustrating adaptive PG/PS controller response throughout a 1000 sec trial. The adaptive PG/PS controller responded to an elevated etCO$_2$ ((orange) empty circles) by dictating a ventilatory pattern with high minute ventilation ((gray) curve labeled as "minute ventilation"). This in turn causes a decrease in etCO$_2$ towards normocapnia. Throughout the trial, iRMSE ((black) solid circles) remained low (<10%), showing that the PS controller was able to match the pattern dictated by the PG.
FIG. 5d shows a plot of etCO$_2$ (in mmHg), illustrating that the adaptive PG/PS controller was able to significantly decrease etCO$_2$.
FIG. 5e shows a plot of iRMSE (in %) versus cycle number, illustrating that the adaptive PG/PS controller was able to maintain low iRMSE after anesthesia-induced hypoventilation (n=6). One trial (rat #6; the (cyan) curve with the highest iRMSE values) showed elevated iRMSE due to loss of entrainment. A low tidal volume resulted from low etCO$_2$, decreasing likelihood of entrainment. The (black) curve with an iRMSE of about 12% at cycle 500 denotes the average iRMSE across all animals.

Adaptive closed-loop pacing alleviated hypercapnia in animals with anesthesia-induced respiratory depression. Anesthesia caused hypoventilation as shown by the increased $etCO_2$ in FIG. 5a. FIG. 5b shows how the adaptive closed-loop controller automatically altered respiratory rate and breath volume in response to hypercapnia and adapted stimulation to account for dynamic changes in the desired ventilatory pattern throughout the trial. In response to elevated $etCO_2$, initially the controller elicited high minute ventilation, which led to a drop in $etCO_2$. As the trial progressed, the controller adapted and responded to a decrease in $etCO_2$ with reduced minute ventilation, eventually leading to and maintaining normocapnia (FIG. 5c). The adaptive PG/PS controller maintained a low iRMSE throughout the trial, confirming that the PS module was able to evoke the desired ventilatory pattern set by the PG module.

A summary of the effects of pacing on $etCO_2$ and iRMSE across all animals is presented in FIG. 5d and FIG. 5e, respectively. Overall, $etCO_2$ decreased by 7.8±2.6 mmHg (p=0.0031) from when the controller was enabled to the end of the trial. An average iRMSE of 13.64±1.44% after entrainment also shows that the PS module adapted. Overall, the PG/PS controller produced an adequate ventilatory pattern to restore regular ventilatory capabilities after reduced ventilatory drive due to central respiratory depression.

Example 3—Restoring Normocapnia after Trauma-Induced Hypoventilation

Figure 6A:
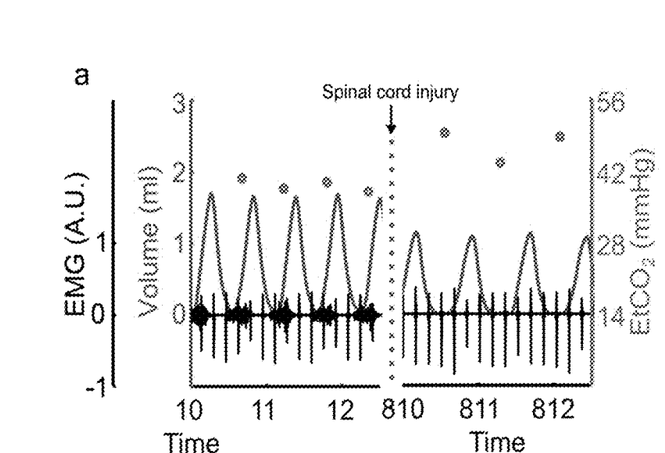
FIG. 6a shows a plot of volume (in ml; left y-axis) and etCO$_2$ (in mmHg; right y-axis) versus time (in s), illustrating breath volume ((blue) curved line), peak etCO$_2$ (empty circles), and diaphragm electromyography (EMG) ((black) lines) in rats with intact spinal cord (left of the dotted "spinal cord injury" vertical line) and after C2 spinal cord hemisection (right of the dotted "spinal cord injury" vertical line). Hemisection of the spinal cord at the C2 level leads to paralysis of the hemidiaphragm ipsilateral to the injury as seen by a lack of bursts of EMG activity following SCI. This leads to hypoventilation and, consequently, to an increase in etCO$_2$. Spikes in the EMG trace reflect artifacts from cardiac activity.
Figure 6B:
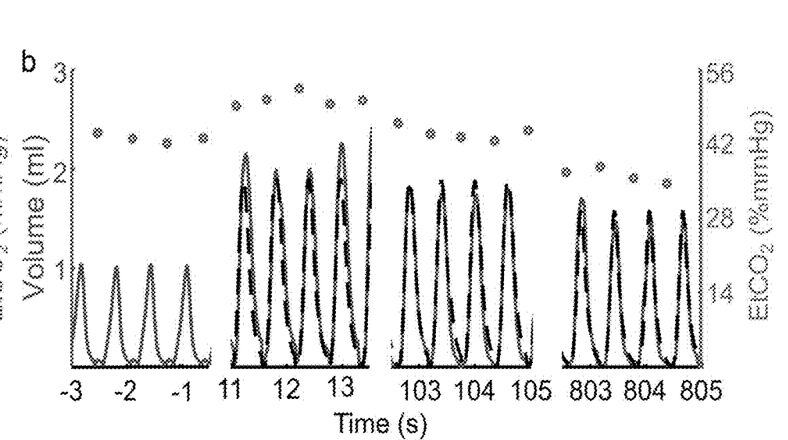
FIG. 6*b* shows a plot of volume (in ml; left y-axis) and etCO$_2$ (in mmHg; right y-axis) versus time (in s), illustrating that after initiation, the adaptive PG/PS controller generated a desired ventilatory pattern ((black) dashed line) with elevated breath volume and shorter breath duration due to elevated etCO$_2$. The PS then attempted to match the measured volume ((blue) solid line) to the desired ventilatory pattern. At 100 sec, the PS was able to match the measured breath profile to the desired breath profile, consequently causing a decrease in the etCO$_2$ ((orange) empty circles). By the end of the trial at 800 sec, etCO$_2$ was within a normocapnic range. Simultaneously, the desired tidal volume and respiratory rate generated by the computational model had decreased and the PS had adapted to match the measured tidal volume profile and respiratory rate to these.
Figure 6C:
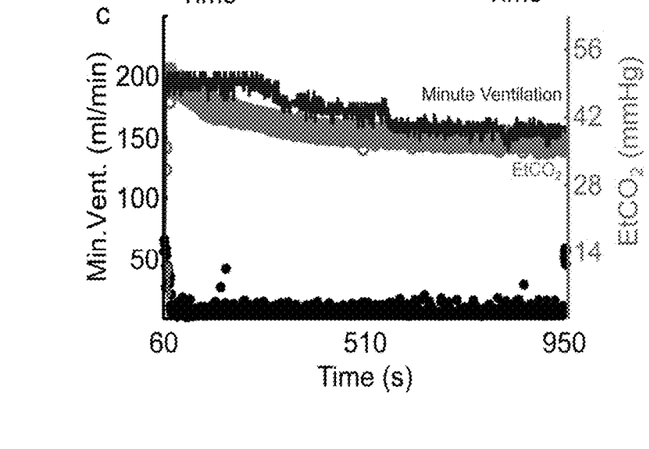
FIG. 6*c* shows a plot of minute ventilation (in milliliters per minute (ml/min); left y-axis) and etCO$_2$ (in mmHg; right y-axis) versus time (in s), illustrating that throughout the trial, the PG/PS controller was able to modulate stimulation parameters, as shown by the low iRMSE ((black) solid circles), to elicit sufficient minute ventilation ((grey) line labeled "minute ventilation") to reduce etCO$_2$ ((orange) empty circles) to normocapnic values. After etCO$_2$ was within the normocapnic range, ventilation was reduced and normocapnia was maintained for the rest of the trial.

In animals with SCI-induced hypoventilation, the PG/PS-controlled pacing achieved normocapnia by prescribing and generating an appropriate ventilatory pattern. A comparison of the ventilatory pattern and ipsilateral diaphragm electromyogram (EMG) before and after SCI is shown in FIG. 6a. FIG. 6b shows how the PG/PS controller responded at the start of the trial, shortly after entrainment onset, and at the end of the trial. After initiation, the adaptive PG/PS controller elicited tidal volumes similar to or larger than those observed prior to injury. This increased tidal volume, coupled with decreased respiratory cycle duration led to an increase in minute ventilation and a decrease in $etCO_2$. Once $etCO_2$ decreased, the PG/PS controller updated the desired ventilatory pattern to maintain normocapnia. FIG. 6c shows that the controller continuously modulated minute ventilation throughout the trial in response to $etCO_2$ values and elicited breaths that matched the desired profile as shown by the low average iRMSE (9.1±3.4%).

Figure 6D:
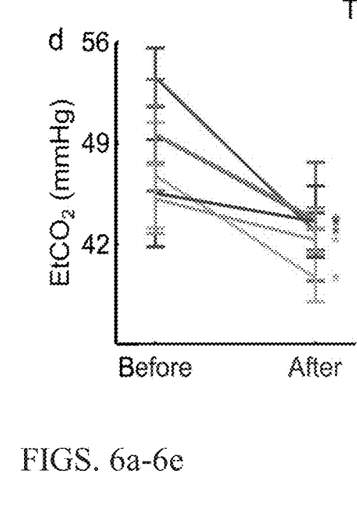
FIG. 6*d* shows a plot of etCO$_2$ (in mmHg), illustrating that the adaptive PG/PS controller was able to restore ventilatory function and reduce etCO$_2$ significantly across all C2 spinal cord hemisected animals.
Figure 6E:
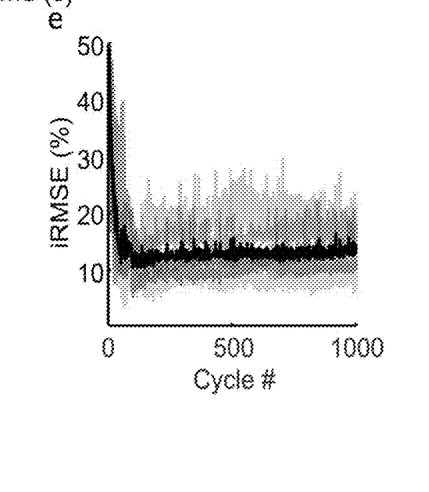
FIG. 6*e* shows a plot of iRMSE (in %) versus cycle number, illustrating that the adaptive PG/PS controller was able to maintain low iRMSE across all animals. The (black) curve with an iRMSE of about 12% at cycle 500 denotes the average iRMSE across all animals.

Across all SCI animals (FIG. 6d), the PG/PS controller was able to reduce $etCO_2$ after onset of pacing and prior to the end of the trial from an average of 50.6±5.7 mmHg to 43.1±2.9 mmHg (p=0.0064). The low average iRMSE (12.35±1.97%) shown in FIG. 6e after entrainment in the SCI animals shows that the controller matched the inspiratory volume profile to the desired profile. This demonstrates that the adaptive controller is able to both determine and provide adequate respiratory pacing when endogenous activation of the diaphragm is impaired after SCI. Below is a discussion on the results of Examples 1-3

Related art diaphragm pacing approaches use manually selected "fixed settings"; there are no related art closed-loop respiratory pacing paradigms that can specify stimulation patterns in an automated fashion and adapt them to meet changing metabolic demands. The adaptive PG/PS closed-loop controller tested in the examples was designed to respond to abnormal $etCO_2$ by adaptively modulating diaphragm muscle activation such that normocapnia can be achieved and maintained.

A computational testbed was used to select controller parameters and to test the ability of the PG/PS controller to respond to dynamic alterations in $PaCO_2$ prior to experimental in vivo assessment. In simulations of changes in $PaCO_2$ levels, the PG/PS controller with adaptation enabled was able to maintain arterial normocapnia over a wider range of metabolic demand than with adaptation disabled, thus demonstrating the value of modulating the ventilatory pattern.

The use of computational testbeds for development and testing of closed-loop neurotechnologies has seen rapid growth as it allows for relatively rapid testing and subsequent deployment of control algorithms prior to in vivo studies in a controlled and predictable environment and they are now being considered as a valuable regulatory tool. In embodiments of the subject invention, a computational testbed was particularly useful for the development of the chemoreceptor response algorithm. By simulating the effects of a sudden change in $CO_2$ production and apneic events, it was possible to minimize their effect on controller stability by introducing an EMA with an appropriate time constant.

A computational approach could also facilitate stimulation of abdominal muscles to effect active expiration. This could be implemented using an rCPG model that includes active expiration and an additional PS module dedicated to control of abdominal musculature for use in an agonist/antagonist manner (see also Fairchild et al., supra.; and Kim et al., Adaptive control of movement for neuromuscular stimulation-assisted therapy in a rodent model, IEEE Trans. Biomed. Eng. 56, 452-461 (2009); which is hereby incorporated by reference herein in its entirety). A computational approach could serve as a viable testbed for such additional functions.

In vivo experiments (Examples 2 and 3), hypoventilation was induced via anesthesia or SCI. The adaptive closed-loop controller was able to increase ventilation and decrease $etCO_2$ in both experimental groups via diaphragmatic pacing. This was successfully accomplished, without user intervention, despite hypoventilation through two different mechanisms, one in which respiratory rate had the largest influence in the reduction of minute ventilation (isoflurane-induced), and another in which reduced tidal volume was the largest factor (SCI-induced). In the former, the adaptive controller was able to cause entrainment of the intrinsic respiratory drive and elevate respiratory rate to mimic an adequate hypercapnic response by adjusting the respiratory cycle duration. Respiratory entrainment to the adaptive controller is likely to have occurred by activating pulmonary stretch receptors and engaging the Hering-Breuer reflex, though it is also possible that intact afferent pathways may have affected intrinsic respiratory drive. In the SCI group, the controller responded to the disruption of ipsilateral respiratory drive by adaptively modulating stimulation to bilaterally control the hemiparetic diaphragm to adjust breath volume.

Related art systems cannot sample and measure $PaCO_2$ in real-time and thereby enable arterial blood gas data to drive the PG/PS controller. However, while it is not an ideal replacement, $etCO_2$ may be used to approximate $PaCO_2$ under certain conditions and is commonly measured in clinical settings to guide medical decisions using standard technology. However, under certain clinical conditions, the correlation between $etCO_2$ and $PaCO_2$ may decrease. Usage of the adaptive controller under such circumstances would need to be more closely monitored and assessed to ensure adequate ventilation is being delivered. Therefore, $etCO_2$ may be used as a practical and effective solution for clinical implementation of the PG/PS controller compared to any existing related art system or method. Other considerations for clinical deployment are the effect of stimulation-induced diaphragm fatigue or compromised efficacy of complementary inspiratory muscles, such as after SCI. Co-stimulation of the intercostal muscles with the diaphragm could more effectively elicit the higher tidal volumes prescribed by the PG during elevated hypercapnia and reduce the work required from the diaphragm, thereby mitigating diaphragm muscle fatigue.

The ability to restore appropriate ventilation under two different mechanisms (respiratory depression and SCI) highlights the versatility of the adaptive PG/PS closed-loop approach of embodiments of the subject invention, and its potential for applicability to the clinical setting where hypoventilation may result from a variety of ventilatory impairments. The data in Examples 1-3 further support the potential use of the controller in respiratory pacing applications to ensure adequate ventilatory function in response to dynamic changes in metabolic demand and/or lung/chest wall properties.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for providing respiratory pacing to meet metabolic needs of a subject, the system comprising:
   a stimulator configured to be in operable communication with the subject; and
   a controller in operable communication with the stimulator and having a pattern generator (PG)/pattern shaper (PS) architecture,
   the controller comprising:
      a processor; and
      a machine-readable medium in operable communication with the processor and having instructions stored thereon that, when executed by the processor, perform the following steps:
         a) collecting, by the processor, first data regarding an end-tidal carbon dioxide ($etCO_2$) level of the subject;
         b) generating, by the processor, a prescribed ventilatory pattern based on the $etCO_2$ level using at least one model on the first data;
         c) tuning, by the processor, pacing parameters of the stimulator such that an evoked ventilatory pattern of the stimulator is matched to the prescribed ventilatory pattern;
         d) causing, by the processor, the stimulator to provide the prescribed ventilatory pattern to the subject; and
         e) repeating steps a)-d) for each breath of the subject while the system is in use, and
      the at least one model comprising at least one of a respiratory central pattern generator (rCPG) model, a pulmonary stretch receptor (PSR) model, and a $CO_2$ chemoreceptor model.

2. The system according to claim 1, the at least one model utilizing at least one of machine learning and a learning algorithm.

3. The system according to claim 1, the at least one model comprising the rCPG model, the PSR model, and the $CO_2$ chemoreceptor model.

4. The system according to claim 3, the chemoreceptor model converting the $etCO_2$ level to neural $CO_2$ drive and providing the neural $CO_2$ drive to the rCPG,
   the rCPG providing simulated inspiratory activity to the PSR, and
   the PSR providing a PSR drive value to the rCPG.

5. The system according to claim 1, the causing of the stimulator to provide the prescribed ventilatory pattern to the subject comprising causing the stimulator to provide the prescribed ventilatory pattern to a diaphragm of the subject.

6. The system according to claim 1, the pacing parameters of the stimulator being tuned only automatically by the controller, with no manual tuning of the pacing parameters of the stimulator while the system is in use.

7. The system according to claim 1, the generating of the prescribed ventilatory pattern comprising:
   generating a ventilatory response based on the $etCO_2$ level using the at least one model on the first data; and
   scaling the ventilatory response in amplitude by a first factor and in time by a second factor to generate the prescribed ventilatory pattern.

8. The system according to claim 1, steps a)-d) occurring in real time.

9. The system according to claim 1, the instructions when executed by the processor further performing the following steps:
   collecting, by the processor, second data regarding a breath volume of the subject; and
   utilizing the second data during the tuning of the pacing parameters of the stimulator.

10. A method for providing respiratory pacing to meet metabolic needs of a subject using a controller having a pattern generator (PG)/pattern shaper (PS) architecture, the method comprising:
   a) collecting, by a processor of the controller in operable communication with a stimulator configured to be in operable communication with the subject, first data regarding an end-tidal carbon dioxide ($etCO_2$) level of the subject;
   b) generating, by the processor, a prescribed ventilatory pattern based on the $etCO_2$ level using at least one model on the first data;
   c) tuning, by the processor, pacing parameters of the stimulator such that an evoked ventilatory pattern of the stimulator is matched to the prescribed ventilatory pattern;
   d) causing, by the processor, the stimulator to provide the prescribed ventilatory pattern to the subject; and
   e) repeating steps a)-d) for each breath of the subject while the method is being performed,
   the at least one model comprising at least one of a respiratory central pattern generator (rCPG) model, a pulmonary stretch receptor (PSR) model, and a $CO_2$ chemoreceptor model.

11. The method according to claim 10, the at least one model comprising the rCPG model, the PSR model, and the $CO_2$ chemoreceptor model.

12. The method according to claim 11, the chemoreceptor model converting the $etCO_2$ level to neural $CO_2$ drive and providing the neural $CO_2$ drive to the rCPG,
   the rCPG providing simulated inspiratory activity to the PSR, and
   the PSR providing a PSR drive value to the rCPG.

13. The method according to claim 10, the causing of the stimulator to provide the prescribed ventilatory pattern to the subject comprising causing the stimulator to provide the prescribed ventilatory pattern to a diaphragm of the subject.

14. The method according to claim 10, the pacing parameters of the stimulator being tuned only automatically by the controller, with no manual tuning of the pacing parameters of the stimulator while the method is being performed.

15. The method according to claim 10, the generating of the prescribed ventilatory pattern comprising:
   generating a ventilatory response based on the $etCO_2$ level using the at least one model on the first data; and
   scaling the ventilatory response in amplitude by a first factor and in time by a second factor to generate the prescribed ventilatory pattern.

16. The method according to claim 10, steps a)-d) occurring in real time.

17. The method according to claim 10, further comprising:
   collecting, by the processor, second data regarding a breath volume of the subject; and
   utilizing the second data during the tuning of the pacing parameters of the stimulator.

18. A system for providing respiratory pacing to meet metabolic needs of a subject, the system comprising:
   a stimulator configured to be in operable communication with the subject; and
   a controller in operable communication with the stimulator and having a pattern generator (PG)/pattern shaper (PS) architecture, the controller comprising:
  a processor; and
  a machine-readable medium in operable communication with the processor and having instructions stored thereon that, when executed by the processor, perform the following steps:
    a) collecting, by the processor, first data regarding an end-tidal carbon dioxide ($etCO_2$) level of the subject;
    b) generating, by the processor, a ventilatory response based on the $etCO_2$ level using at least one model on the first data;
    c) scaling, by the processor, the ventilatory response in amplitude by a first factor and in time by a second factor to generate a prescribed ventilatory pattern;
    d) collecting, by the processor, second data regarding a breath volume of the subject;
    e) tuning, by the processor, pacing parameters of the stimulator, utilizing the second data, such that an evoked ventilatory pattern of the stimulator is matched to the prescribed ventilatory pattern;
    f) causing, by the processor, the stimulator to provide the prescribed ventilatory pattern to a diaphragm of the subject; and
    g) repeating steps a)-f) for each breath of the subject while the system is in use,
  the at least one model comprising a respiratory central pattern generator (rCPG) model, a pulmonary stretch receptor (PSR) model, and a $CO_2$ chemoreceptor model,
  the chemoreceptor model converting the $etCO_2$ level to neural $CO_2$ drive and providing the neural $CO_2$ drive to the rCPG,
  the rCPG providing simulated inspiratory activity to the PSR,
  the PSR providing a PSR drive value to the rCPG,
  the pacing parameters of the stimulator being tuned only automatically by the controller, with no manual tuning of the pacing parameters of the stimulator while the system is in use, and
  steps a)-f) occurring in real time.

* * * * *